(12) United States Patent
Rupp et al.

(10) Patent No.: US 11,090,105 B2
(45) Date of Patent: *Aug. 17, 2021

(54) ANCILLARY CIRCUIT TO INDUCE ZERO VOLTAGE SWITCHING IN A POWER CONVERTER

(71) Applicant: Covidien LP, Mansfield, MA (US)

(72) Inventors: Steven C. Rupp, Arvada, CO (US);
Robert B. Smith, Loveland, CO (US);
Daniel A. Friedrichs, Aurora, CO (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/699,854

(22) Filed: Dec. 2, 2019

(65) Prior Publication Data

US 2020/0100831 A1 Apr. 2, 2020

Related U.S. Application Data

(63) Continuation of application No. 15/150,512, filed on May 10, 2016, now Pat. No. 10,492,848.

(51) Int. Cl.
*A61B 18/12* (2006.01)
*H02M 3/158* (2006.01)
(Continued)

(52) U.S. Cl.
CPC ......... *A61B 18/1206* (2013.01); *H02M 3/158* (2013.01); *A61B 18/14* (2013.01);
(Continued)

(58) Field of Classification Search
CPC .......... H02M 2001/0058; H02M 3/156–1588; A61B 2018/1266; A61B 2018/1286;
(Continued)

(56) References Cited

U.S. PATENT DOCUMENTS

| | | |
|---|---|---|
| 5,173,846 A | 12/1992 | Smith |
| 5,305,191 A | 4/1994 | Loftus, Jr. |

(Continued)

FOREIGN PATENT DOCUMENTS

| | | |
|---|---|---|
| GB | 2265771 | 10/1993 |
| WO | 2015105795 | 7/2015 |
| WO | 2017117367 | 7/2017 |

OTHER PUBLICATIONS

European Search Report dated Sep. 27, 2017 issued in corresponding European Patent Application No. 17170056.0.

(Continued)

*Primary Examiner* — Jaymi E Della
*Assistant Examiner* — Sean W Collins
(74) *Attorney, Agent, or Firm* — Carter, DeLuca & Farrell LLP

(57) ABSTRACT

An electrosurgical generator includes a power supply configured to output a DC waveform, a current or voltage source coupled to the power supply and a power converter coupled to the current or voltage source, the power converter including at least one power switching element and a power inductor having an inductance value during switching of the at least one power switching element. The electrosurgical generator further includes a zero voltage switching (ZVS) inducing circuit coupled to the power converter at a switching node, the ZVS inducing circuit including an inductor having an inductance which is greater than the inductance value of the power inductor of the at least one power switching element.

16 Claims, 6 Drawing Sheets

(51) Int. Cl.
*H02M 1/00* (2006.01)
*A61B 18/00* (2006.01)
*A61B 18/14* (2006.01)
*A61B 18/16* (2006.01)

(52) U.S. Cl.
CPC ....... *A61B 18/16* (2013.01); *A61B 2018/0063* (2013.01); *A61B 2018/0072* (2013.01); *A61B 2018/00577* (2013.01); *A61B 2018/00589* (2013.01); *A61B 2018/00601* (2013.01); *A61B 2018/00767* (2013.01); *A61B 2018/00994* (2013.01); *A61B 2018/1286* (2013.01); *H02M 2001/0058* (2013.01); *Y02B 70/10* (2013.01)

(58) Field of Classification Search
CPC ............ A61B 18/1206; A61B 18/1233; A61B 2018/1213–1226; A61B 2018/00767; A61B 2018/0072; A61B 2018/1273; A61B 2018/1293; A61B 2018/1823; Y02B 70/1491
See application file for complete search history.

(56) References Cited

U.S. PATENT DOCUMENTS

| | | |
|---|---|---|
| 5,836,943 A | 11/1998 | Miller, III |
| 5,880,940 A | 3/1999 | Poon |
| 6,008,630 A | 12/1999 | Prasad |
| 6,359,793 B2 | 3/2002 | Lee |
| 6,614,288 B1 | 9/2003 | Dagan et al. |
| 6,987,675 B2 | 1/2006 | Jovanovic et al. |
| 7,019,988 B2 | 3/2006 | Fung et al. |
| 7,375,984 B2 | 5/2008 | Lee |
| 7,551,459 B1 | 6/2009 | Wittenbreder, Jr. |
| 2004/0066178 A1 | 4/2004 | Mizoguchi et al. |
| 2005/0190582 A1 | 9/2005 | Jacobs |
| 2012/0014150 A1 | 1/2012 | Domb |
| 2012/0127769 A1 | 5/2012 | Kern |
| 2014/0153288 A1 | 6/2014 | Yonezawa |

OTHER PUBLICATIONS

European Search Report dated Nov. 2, 2018 issued in corresponding EP Appln. No. 17170056.0.
European Examination Report dated Nov. 2, 2018 issued in corresponding EP Appln. No. 17170056.0.

ANCILLARY CIRCUIT TO INDUCE ZERO VOLTAGE SWITCHING IN A POWER CONVERTER

CROSS-REFERENCE TO RELATED APPLICATIONS

This application is a continuation of U.S. patent application Ser. No. 15/150,512, filed on May 10, 2016. The entire disclosure of the foregoing application is incorporated by reference herein.

BACKGROUND

Technical Field

The present disclosure relates to systems and methods for controlling an electrosurgical generator. In particular, the present disclosure relates to an electrosurgical generator including an ancillary circuit for inducing zero voltage switching in a power converter.

Background of Related Art

Electrosurgery involves application of high radio frequency electrical current to a surgical site to cut, ablate, desiccate, or coagulate tissue. In monopolar electrosurgery, a source or active electrode delivers radio frequency alternating current from the electrosurgical generator to the targeted tissue. A patient return electrode is placed remotely from the active electrode to conduct the current back to the generator.

In bipolar electrosurgery, return and active electrodes are placed in close proximity to each other such that an electrical circuit is formed between the two electrodes (e.g., in the case of an electrosurgical forceps). In this manner, the applied electrical current is limited to the body tissue positioned between the electrodes. Accordingly, bipolar electrosurgery generally involves the use of instruments where it is desired to achieve a focused delivery of electrosurgical energy between two electrodes.

Conventional electrosurgical generators may utilize voltage-fed or current-fed power converters. Current-fed power converters have a number of advantages over voltage-fed converters including control of arcs, desirable transient performance, and simplified control dynamics. However, current-fed power converters also present a number of issues, such as power dissipation, which limits their usability. Accordingly, there is a need for a system and method to control an electrosurgical generator including a current-fed power converter that overcomes these issues.

SUMMARY

The present disclosure provides for an electrosurgical generator including a power converter having a plurality of switching elements, such as transistors, which produces therapeutic radio-frequency energy. The generator also includes a current or voltage source and an ancillary circuit. The current or voltage source supplies current or voltage to the radio-frequency power converter, whereas the ancillary circuit mitigates some of the effects of the current or voltage source on the power converter to achieve zero voltage switching therein.

Electrosurgical generators according to the present disclosure may include voltage-fed converters having one or more switching elements, which operate based on switching on/off of the switching-elements to control the power. Electrosurgical generators according to the present disclosure may also include current-fed converters, which control power delivery by shorting the current to ground, or some other return path. Thus, when the voltage-fed converter turns on all of the switching elements, this results in large power dissipation with potentially destructive currents. To deal which these surges, at least one of the switching elements must be open or off at all times. For the current-fed converter, shorting or shunting the current source, e.g., an inductor, no significant power is dissipated while the current flow is maintained.

The generator according to the present disclosure includes non-resonant architecture and hence, does not require tuned output filtering. The generator may include a power converter which is input power limited. The generator according to the present disclosure may also include either a current-fed or voltage-fed topology and a current source (e.g., an inductance) coupled to the power converter.

According to one embodiment of the present disclosure, an electrosurgical generator is disclosed. The electrosurgical generator includes a power supply configured to output a DC waveform and a power converter coupled to the power supply, the power converter including at least one power switching element and a power inductor having an inductance value during switching of the at least one power switching element. The electrosurgical generator further includes a zero voltage switching (ZVS) inducing circuit coupled to the power converter at a switching node, the ZVS inducing circuit including an inductor having an inductance which is greater than the inductance value of the power inductor during switching of the at least one power switching element.

According to one aspect of any of the above embodiments, the ZVS inducing circuit is a low voltage circuit configured to return voltage to the at least one switching element of the power converter to zero.

According to another aspect of any of the above embodiments, the ZVS inducing circuit further includes a zero voltage diode, a first zero voltage switching element, and a second zero voltage switching element.

According to a further aspect of any of the above embodiments, the second zero voltage switching element couples the inductor to the zero voltage diode.

According to a further aspect of any of the above embodiments, the inductor is coupled between the first and second zero voltage switching elements.

According to a further aspect of any of the above embodiments, the zero voltage diode is configured to store current in the inductor, in response to the first and second zero voltage switching elements being energized.

According to a further aspect of any of the above embodiments, the inductor is configured to provide current to the switching node of the power converter from the zero voltage diode, in response to the second zero voltage switching element and at least one of the power switching elements of the power converter being de-energized.

According to a further aspect of any of the above embodiments, the inductor supplies excess current flowing therethrough to the power supply connected to the at least one power switching element, in response to the switch node voltage of the switching node being increased.

According to one embodiment of the present disclosure, an electrosurgical generator is disclosed. The electrosurgical generator includes a power supply configured to output a DC waveform and a power converter coupled to the power supply, the power converter including a first power switching element, a second power switching element, and a power inductor having an inductance value during switching of the first or second power switching elements. The electrosurgical generator further includes a zero voltage switching (ZVS) inducing circuit coupled to the power converter at a switching node, the ZVS inducing circuit including a zero-voltage inductor having an inductance which is greater that the inductance value of the power inductor during switching of the first or second power switching elements.

According to a further embodiment of the present disclosure, a method for controlling an electrosurgical generator is disclosed. The method includes activating a first power switching element to increase current flowing through a power inductor, deactivating the first power switching element so that the current flows from a second power switching element, the first power switching element, the second power switching element, and the power inductor being part of a power converter, and activating the second power switching element so that the current flows through a conductive channel of the second power switching element to supply the current of the power inductor. The method further includes activating a first zero voltage switching element and a second zero voltage switching element of a zero voltage switching (ZVS) inducing circuit coupled to the power converter at a switching node to increase current flowing through an inductor of the ZVS inducing circuit, deactivating the second zero voltage switching element of the ZVS inducing circuit, deactivating the second power switching element of the power converter, and feeding the current flowing through the inductor, via a zero voltage switching diode, to the switching node to increase a switch node voltage until excess current flowing through the inductor is supplied to a power supply connected to the first power switching element.

BRIEF DESCRIPTION OF THE DRAWINGS

The present disclosure may be understood by reference to the accompanying drawings, when considered in conjunction with the subsequent, detailed description, in which.

DETAILED DESCRIPTION

Particular embodiments of the present disclosure will be described below with reference to the accompanying drawings. In the following description, well-known functions or constructions are not described in detail to avoid obscuring the present disclosure in unnecessary detail. Those skilled in the art will understand that the present disclosure may be adapted for use with any of an endoscopic instrument, a laparoscopic instrument, or an open instrument. It should also be appreciated that different electrical and mechanical connections and other considerations may apply to each particular type of instrument.

A generator may be used in monopolar and/or bipolar electrosurgical procedures, including, for example, cutting, coagulation, ablation, and vessel sealing procedures. The generator may include a plurality of outputs for interfacing with various ultrasonic and electrosurgical instruments (e.g., ultrasonic dissectors and hemostats, monopolar instruments, return electrode pads, bipolar electrosurgical forceps, footswitches, etc.). Further, the generator may include electronic circuitry configured to generate radio frequency energy specifically suited for powering ultrasonic instruments and electrosurgical devices operating in various electrosurgical modes (e.g., cut, blend, coagulate, division with hemostasis, fulgurate, spray, etc.) and procedures (e.g., monopolar, bipolar, vessel sealing).

Figure 1:
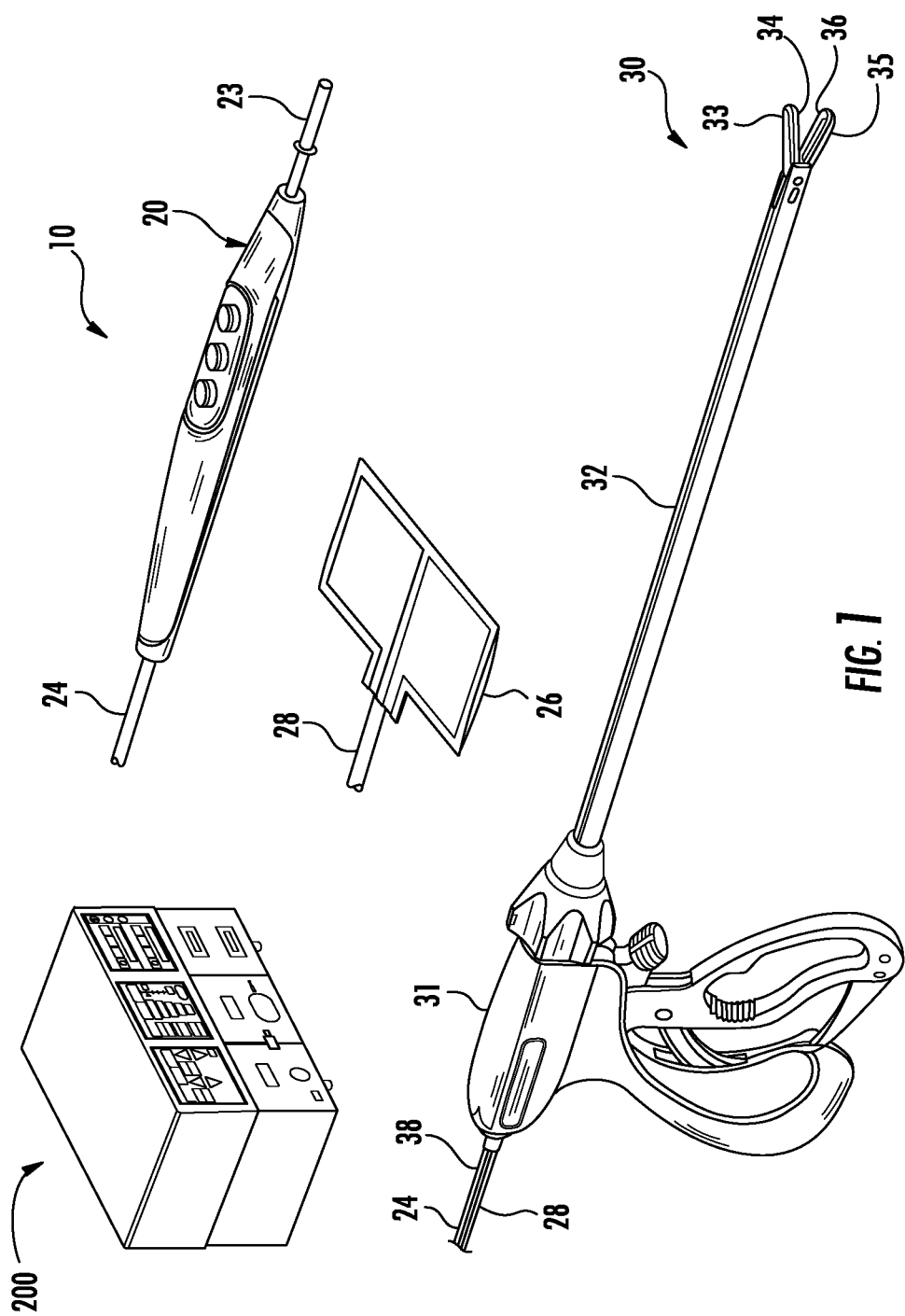
FIG. 1 is a perspective view of a surgical system according to an embodiment of the present disclosure.

Referring to FIG. 1 an electrosurgical system 10 according to the present disclosure is shown which includes a generator 200 and may include one or more monopolar electrosurgical instruments 20 having one or more active electrodes 23 (e.g., electrosurgical cutting probe, ablation electrode(s), etc.) for treating tissue of a patient. Electrosurgical alternating RF current is supplied to the instrument 20 by generator 200 via a supply line 24 that is connected to an active terminal (not shown) of the generator 200, allowing the instrument 20 to cut, coagulate, thermally or non-thermally ablate and/or otherwise treat tissue. The alternating current is returned to the generator 200 through a return electrode pad 26 via a return line 28 at a return terminal (not shown) of the generator 200. For monopolar operation, the system 10 may include a plurality of return electrode pads 26 that, in use, are disposed on a patient to minimize the chances of tissue damage by maximizing the overall contact area with the patient. In addition, the generator 200 and the return electrode pads 26 may be configured for monitoring tissue-to-patient contact to ensure that sufficient contact exists therebetween.

The system 10 may also include one or more bipolar electrosurgical instruments, for example, a bipolar electrosurgical forceps 30 having one or more electrodes for treating tissue of a patient. The electrosurgical forceps 30 includes a housing 31 and opposing jaw members 33 and 35 disposed at a distal end of a shaft 32. The jaw members 33 and 35 have one or more active electrodes 34 and a return electrode 36 disposed therein, respectively. The active electrode 34 and the return electrode 36 are connected to the generator 200 through cable 38 that includes the supply and return lines 24, 28, which may be coupled to the active and return terminals, respectively. The electrosurgical forceps 30 is coupled to the generator 200 at a port having connections to the active and return terminals (e.g., pins) via a plug disposed at the end of the cable 38, wherein the plug includes contacts from the supply and return lines 24, 28 as described in more detail below.

Figure 2:
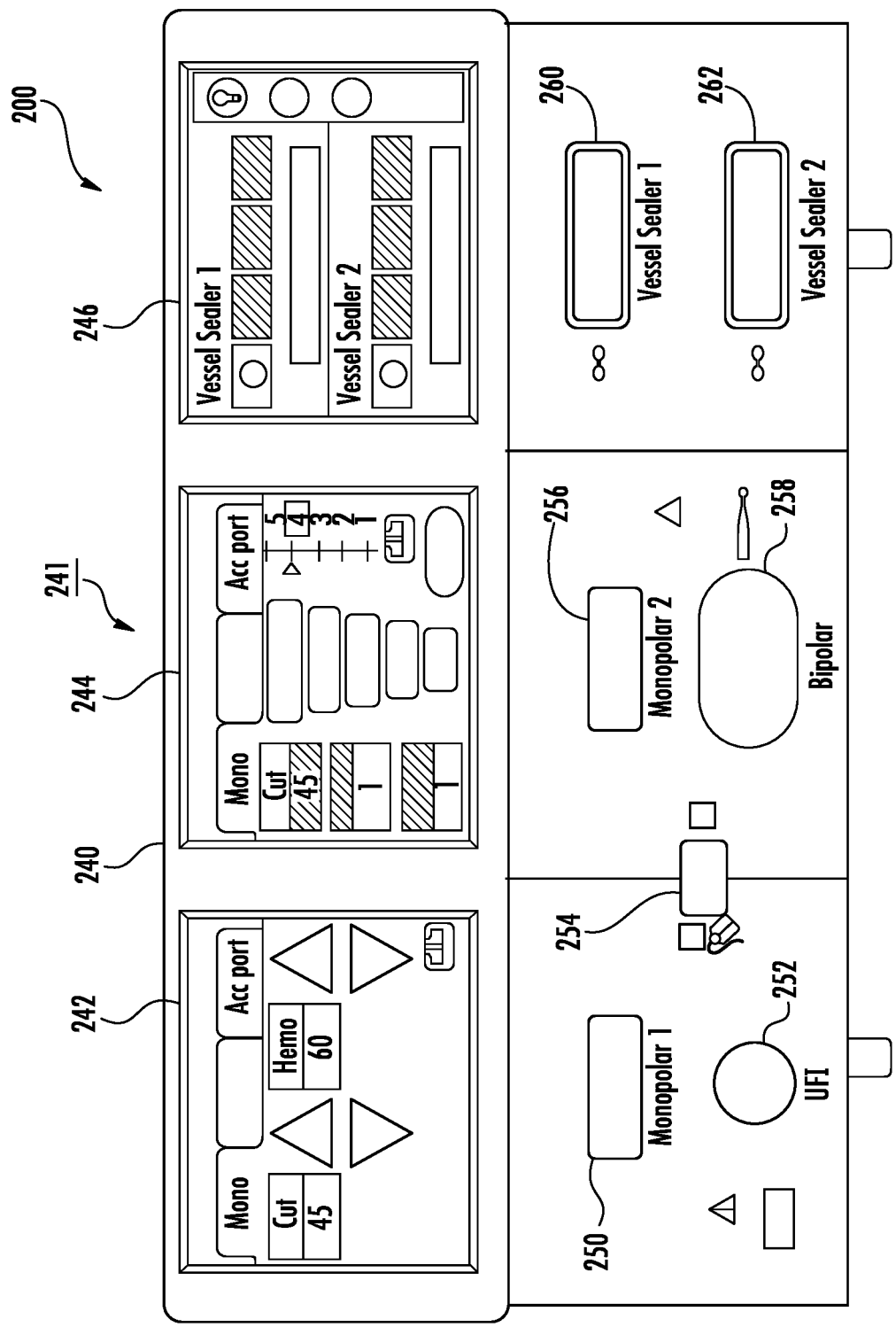
FIG. 2 is a front view of an electrosurgical generator of the surgical system of FIG. 1 according to an embodiment of the present disclosure.

With reference to FIG. 2, a front face 240 of the generator 200 is shown. The generator 200 may include a plurality of ports 250-262 to accommodate various types of electrosurgical instruments (e.g., monopolar electrosurgical instrument 20, electrosurgical forceps 30, etc.).

The generator 200 includes a user interface 241 having one or more display screens 242, 244, 246 for providing the user with variety of output information (e.g., intensity settings, treatment complete indicators, etc.). Each of the screens 242, 244, 246 is associated with a corresponding port 250-262. The generator 200 includes suitable input controls (e.g., buttons, activators, switches, touch screen, etc.) for controlling the generator 200. The screens 242, 244, 246 are also configured as touch screens that display a corresponding menu for the instruments (e.g., electrosurgical forceps 30, etc.). The user then adjusts inputs by simply touching corresponding menu options.

Screen 242 controls monopolar output and the devices connected to the ports 250 and 252. Port 250 is configured to couple to a monopolar electrosurgical instrument (e.g., electrosurgical instrument 20) and port 252 is configured to couple to a foot switch (not shown). The foot switch provides for additional inputs (e.g., replicating inputs of the generator 200). Screen 244 controls monopolar and bipolar output and the devices connected to the ports 256 and 258. Port 256 is configured to couple to other monopolar instruments. Port 258 is configured to couple to a bipolar instrument (not shown).

Screen 246 controls the electrosurgical forceps 30 that may be plugged into one of the ports 260 and 262, respectively. The generator 200 outputs energy through the ports 260 and 262 suitable for sealing tissue grasped by the electrosurgical forceps 30. In particular, screen 246 outputs a user interface that allows the user to input a user-defined intensity setting for each of the ports 260 and 262. The user-defined setting may be any setting that allows the user to adjust one or more energy delivery parameters, such as power, current, voltage, energy, etc. or sealing parameters, such as energy rate limiters, sealing duration, etc. The user-defined setting is transmitted to a controller (not shown) where the setting may be saved in memory. In embodiments, the intensity setting may be a number scale, such as for example, from one to ten or one to five. In embodiments, the intensity setting may be associated with an output curve of the generator 200. The intensity settings may be specific for each electrosurgical forceps 30 being utilized, such that various instruments provide the user with a specific intensity scale corresponding to the electrosurgical forceps 30. The active and return terminals may be coupled to any of the desired ports 250-262. In embodiments, the active and return terminals may be coupled to the ports 250-262.

Figure 3:
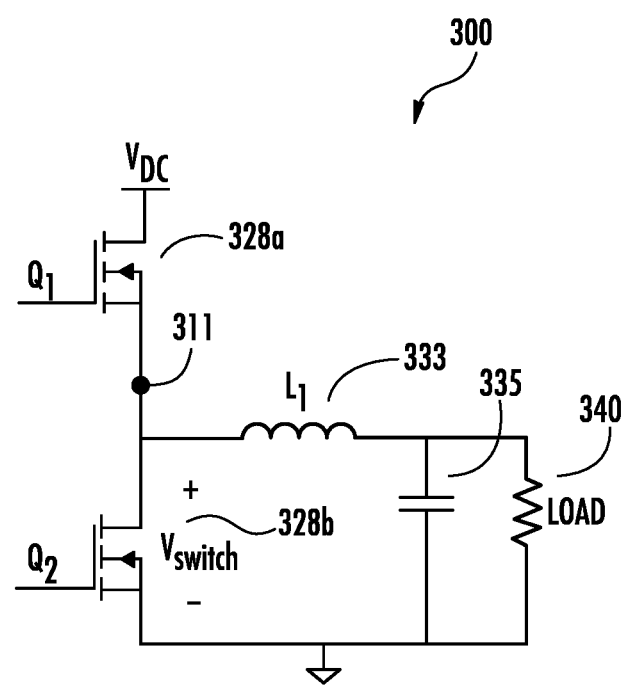
FIG. 3 is a schematic diagram of a power converter.

FIG. 3 is a schematic diagram of a power converter. The power converter 300 may be a buck converter. The elements of the buck converter will be described in detail with reference to FIG. 4. The buck converter may be connected to a controller. The controller may include a processor (not shown) operably connected to a memory (not shown), which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to perform the calculations and/or set of instructions described herein.

Figure 4:
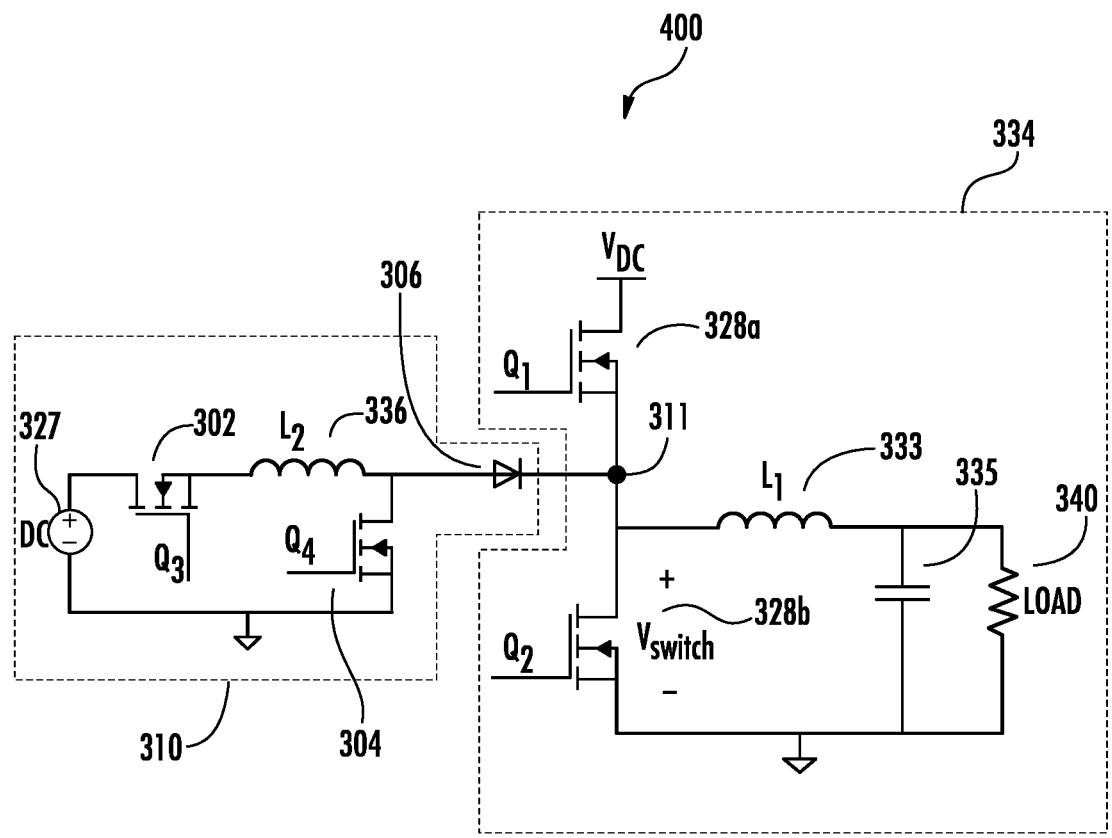
FIG. 4 is a schematic diagram of the electrosurgical generator of FIG. 2 having an ancillary circuit connected to the power converter of FIG. 3, according to the present disclosure.

FIG. 4 is a schematic diagram 400 of the electrosurgical generator of FIG. 2 having an ancillary circuit 310 connected to the power converter 300 of FIG. 3, according to the present disclosure.

The ancillary circuit 310 is a zero voltage switching (ZVS) inducing circuit. The ZVS inducing circuit 310 eliminates the above-described issues with current source generators since the ZVS inducing circuit 310 is a low voltage circuit configured to return voltage at the at least one switching element 328a-b of the power converter 334 to zero. In particular, the ZVS inducing circuit 310 is coupled in series with the power converter 334 at switching node 311. The ZVS inducing circuit 310 is coupled to the power supply 327 for supplying current to the first zero voltage switching element 302 ($Q_3$), the second zero voltage switching element 304 ($Q_4$), and the current source 336. The current source 336 may be an inductor, $L_2$. The ZVS inducing circuit 310 further includes a zero voltage diode 306 connected to the power converter 334 via the switching node 311.

The second zero voltage switching element 304 couples the zero voltage inductor 336 with the zero voltage diode 306. The zero voltage inductor 336 is coupled between the first and second zero voltage switching elements 304, 306. The first and second zero voltage switching elements 304, 306 are configured to be switched at a fixed duty cycle by the controller (not shown) to establish the desired voltage at one or more switching elements of the power converter 334. The desired voltage at the one or more switching elements 328a, 328b of the power converter 334 is controlled by the first and second zero voltage switching elements 304, 306, as well as the zero voltage inductor 336, which aids in producing a zero voltage across one or more switching elements 328a, 328b of the power converter 334.

The first power switching element 328a is a high side voltage switching element, whereas the second power switching element 328b is a low side voltage switching element. The power switching elements 328a, 328b may be transistors, such as field-effect transistors (FETs) or any other suitable type of voltage switching elements as described above.

The power converter 334 further includes a power inductor 333 ($L_1$). The first end of the power inductor 333 is connected in parallel to the first and second power switching elements 328a, 328b. The second end of the power inductor 333 is connected in parallel to a capacitor 335 and a load 340.

In operation, when the first power switching element 328a is turned on or activated, the voltage at the switching node 311 is high and current is ramping up in the power inductor 333. The first power switching element 328a is then turned off, resulting in the voltage at the switching node 311 to rapidly fall to zero due to the current in the power inductor 333. At this time, the current going through the power inductor 333 flows from the body diode of the second power switching element 328b. After a short period of time, the second power switching element 328b is turned on, and current flows through the conductive channel of the second power switching element 328b to supply the requirements of the power inductor 333.

At a predetermined time, or by a time determined by the current flowing through the power converter 333, the first and second zero voltage switching elements 302, 304 are turned on and the current flowing through the zero voltage inductor 336 ramps up. Then, the second zero switching element 304 and the second power switching element 328b are switched off. These switching elements may be turned off at the same time. Alternatively, the second zero voltage switching element 304 may be turned off before the second power switching element 328b. The current flowing through the zero voltage inductor 336 is fed, via the zero voltage diode 306, to the switching node 311. The switch node voltage quickly rises until the excess current from the zero voltage inductor 336 is returned to the supply voltage, $V_DC$, via the body diode of the first power switching element 328a. The first power switching element 328a is then turned on, and the first zero voltage switching element 302 is turned off. The cycle is then complete and repeats itself.

Thus, the ancillary circuit 310 aids in producing a minor or negligible switching loss to be exhibited across the first power switching element 328a. For this low to high voltage commutation to occur at the switching node 311, the current build-up in the zero voltage inductor 336 must be greater than the current build-up at the power inductor 333 of the power converter 334. In other words, the ZVS inducing circuit 310 must include a zero-voltage inductor 336 having greater inductance than the inductance of the power inductor 333 during voltage switching.

Figure 5:
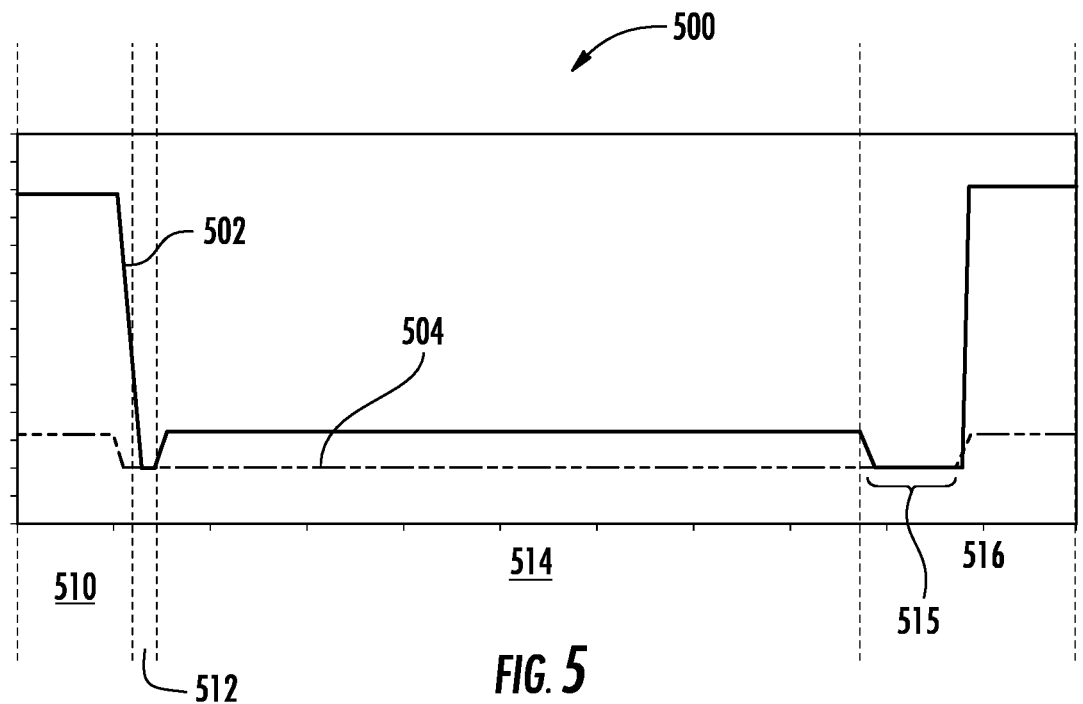
FIG. 5 is a plot of waveforms generated by a power converter without an ancillary circuit.

Referring to FIG. 5, plot 500 represents waveforms generated by a power converter without the ancillary circuit. A first waveform 502 represents the high side power switching element 328a and a second waveform 504 represents the low side power switching element 328b. Initially, during time period 510, the second power switching elements 328b is turned on. In time period 510, the low side power switching element 328b has a higher voltage than the high side power switching element 328a.

At a predetermined time, during time period 512, the low side power switching element 328b is turned off. As a result, the voltage across the low side power switching element 328b drops to zero. During time period 514, current flows through the low side power switching element 328b such that a voltage is present across it. The high side power switching element 328a is turned off. During time period 516, the low side power switching element 328b is turned on. As shown in FIG. 5, a switching loss is exhibited during a time period 515, or $t_1$ when the low side power switching element 328b transitions from a fully-off state to a fully-on state. When the low side power switching element 328b is switched, some amount of power is converted to heat. This power conversion to heat causes a switching delay during time period 515, or $t_1$.

Figure 6:
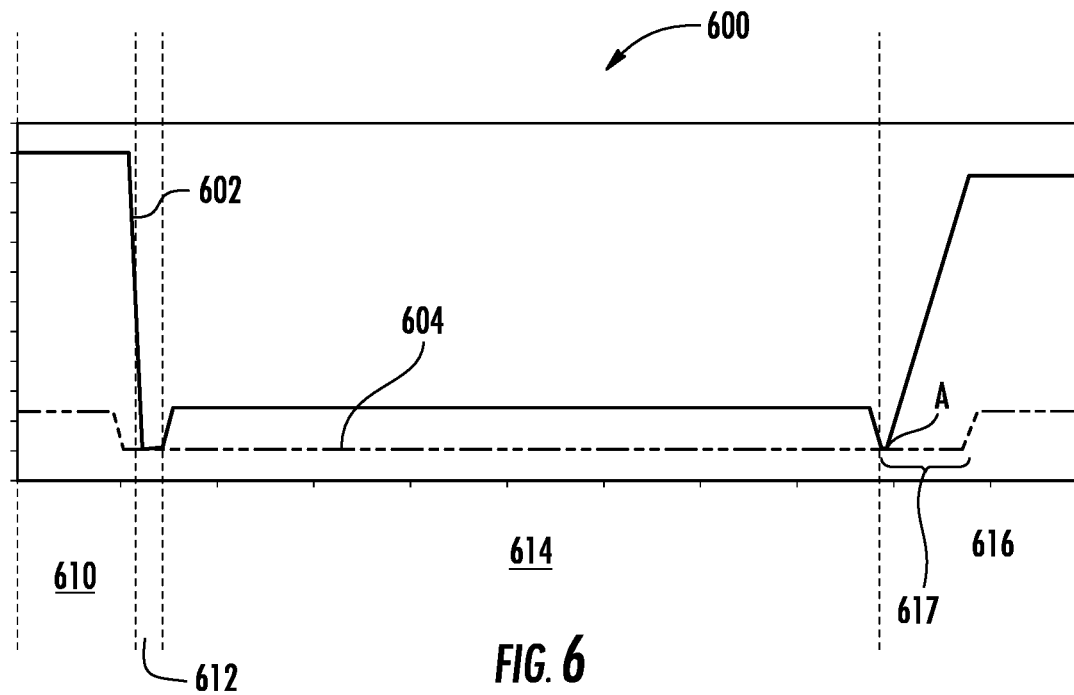
FIG. 6 is a plot of waveforms generated by a power converter with the ancillary circuit of FIG. 4 according to the present disclosure.

Referring to FIG. 6, plot 600 represents waveforms generated by a power converter with the ancillary circuit according to the present disclosure. In order to eliminate the switching loss exhibited in FIG. 5, the ancillary circuit 310 is connected to the power converter 334 (FIG. 4). As shown in FIG. 6, a first waveform 602 represents the high side power switching element 328a and a second waveform 604 represents the low side power switching element 328b. During time periods 610, 612, and 614, the first and second waveforms 602 and 604 look similar to the waveforms 502 and 504 in FIG. 5. However, changes occur during time period 616. At time period 616, the low side power switching element 328b is turned on. Also as shown in FIG. 6, a minor or negligible switching loss is exhibited during a time period 617, or $t_2$ when the low side power switching element 328b transitions from a fully-off state to a fully-on state. Thus, when the low side power switching element 328b is switched, a minor or negligible switching delay occurs during time period 617, or $t_2$. In particular, at point "A," the voltage across the low side power switching element 328b steadily ramps up until it reaches a peak value and maintains such stable level until the next cycle or switching event.

Figure 7:
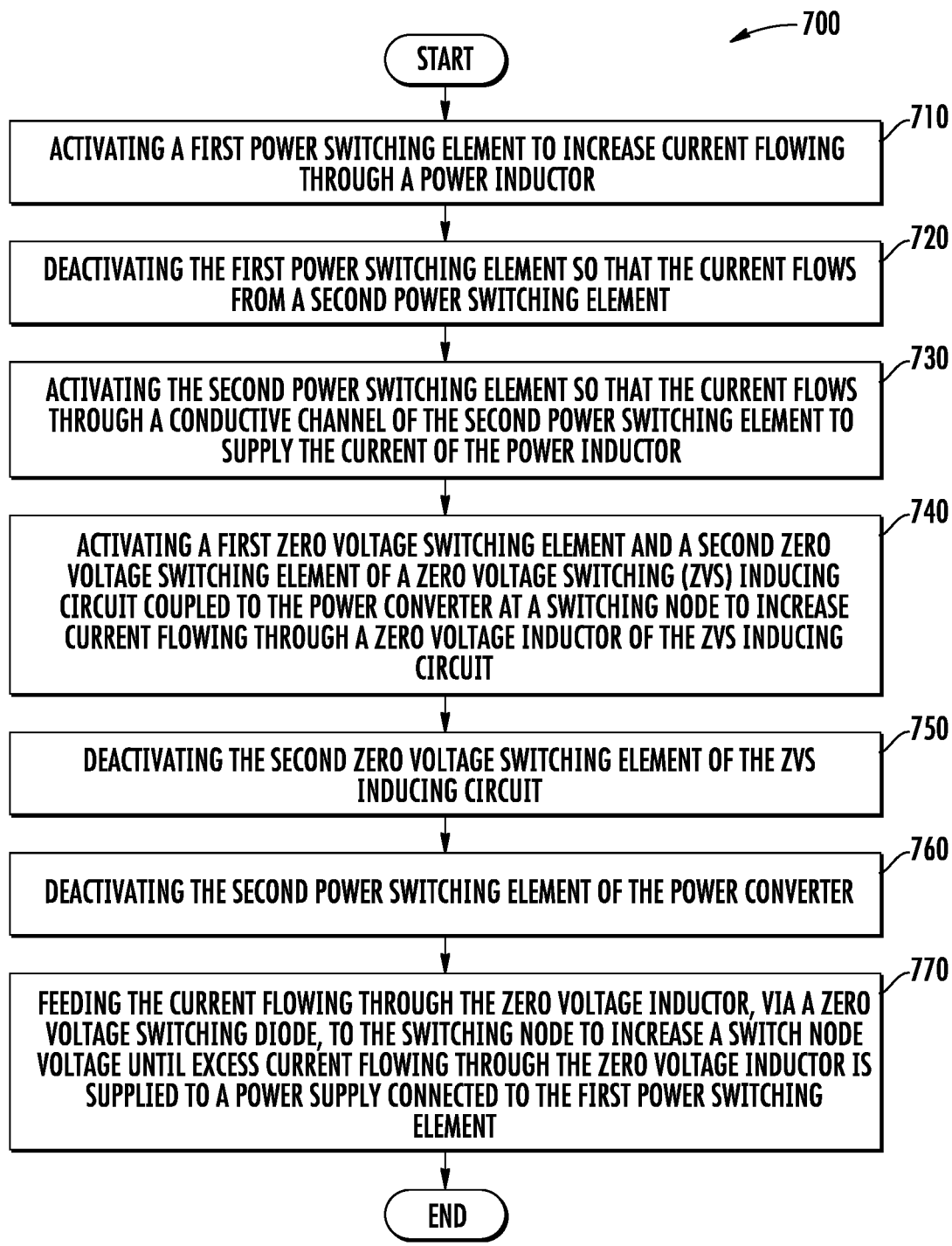
FIG. 7 is a flow chart of a method for operating the electrosurgical generator of FIG. 4 according to an embodiment of the present disclosure.

Referring now to FIG. 7 a flow chart 700 shows a method for operating the electrosurgical generator of FIG. 4 according to an embodiment of the present disclosure. In step 710, a first power switching element is activated to increase current flowing through a power inductor. In step 720, the first power switching element is deactivated so that the current flows from a second power switching element, the first power switching element, the second power switching element, and the power inductor being part of a power converter. In step 730, the second power switching element is activated so that the current flows through a conductive channel of the second power switching element to supply the current of the power inductor. In step 740, a first zero voltage switching element and a second zero voltage switching element of a zero voltage switching (ZVS) inducing circuit are activated, the ZVS inducing circuit coupled to the power converter at a switching node to increase current flowing through a zero voltage inductor of the ZVS inducing circuit. In step 750, the second zero voltage switching element of the ZVS inducing circuit is deactivated. In step 760, the second power switching element of the power converter is deactivated. In step 770, the current flowing through the zero voltage inductor is fed, via a zero voltage switching diode, to the switching node to increase a switch node voltage until excess current flowing through the zero voltage inductor is supplied to a power supply connected to the first power switching element. The process then ends for the first cycle or first iteration. However, the process may be a continuous iterative process. In other words, the steps of the process may repeat for a number cycles or iterations, where parameters of the ZVS inducing circuit are constantly adjusted.

While several embodiments of the disclosure have been shown in the drawings and/or described herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope of the claims appended hereto.

What is claimed is:

1. An electrosurgical generator, comprising:
a power supply configured to output a DC waveform;
a power converter coupled to the power supply, the power converter including at least one power switching element; and
a zero voltage switching (ZVS) inducing circuit coupled to the power converter, the ZVS inducing circuit including:
a ZVS inductor;
a first ZVS element;
a second ZVS element; and
a zero voltage diode configured to store current in the ZVS inductor in response to the first and second ZVS elements being energized.

2. The electrosurgical generator according to claim 1, wherein the ZVS inducing circuit is configured to return voltage to the at least one power switching element of the power converter to zero.

3. The electrosurgical generator according to claim 1, wherein the second ZVS element couples the ZVS inductor to the zero voltage diode.

4. The electrosurgical generator according to claim 1, wherein the ZVS inductor is coupled between the first and second ZVS elements.

5. The electrosurgical generator according to claim 1, wherein the ZVS inductor is configured to provide the current from the zero voltage diode to a switching node at which the ZVS inducing circuit is coupled to the power converter, in response to the second ZVS element and the at least one power switching element of the power converter being de-energized.

6. The electrosurgical generator according to claim 5, wherein the ZVS inductor supplies excess current flowing therethrough to the power supply connected to the at least one power switching element, in response to a switch node voltage of the switching node being increased.

7. The electrosurgical generator according to claim 1, wherein the power converter further includes a power inductor having a first inductance value.

8. The electrosurgical generator according to claim 7, wherein the ZVS inductor has a second inductance that is greater than the first inductance value.

9. An electrosurgical generator, comprising:
a power supply configured to output a DC waveform;
a power converter coupled to the power supply, the power converter including a first power switching element and a second power switching element; and
a zero voltage switching (ZVS) inducing circuit coupled to the power converter, the ZVS inducing circuit including:
a ZVS inductor;
a first ZVS element; and
a second ZVS element; and
a zero voltage diode configured to store current in the ZVS inductor in response to the first and second ZVS elements being energized.

10. The electrosurgical generator according to claim 9, wherein the ZVS inducing circuit is configured to return voltage to the first power switching element of the power converter to zero.

11. The electrosurgical generator according to claim 9, wherein the second ZVS element couples the ZVS inductor to the zero voltage diode.

12. The electrosurgical generator according to claim 9, wherein the ZVS inductor is coupled between the first and second ZVS elements.

13. The electrosurgical generator according to claim 9, wherein the ZVS inductor is configured to provide the current from the zero voltage diode to a switching node at which the ZVS inducing circuit is coupled to the power converter, in response to the second ZVS element and at least one of the first power switching element or the second power switching element of the power converter being de-energized.

14. The electrosurgical generator according to claim 13, wherein the ZVS inductor supplies excess current flowing therethrough to the power supply connected to at least one of the first power switching element or the second power switching element, in response to a switch node voltage of the switching node being increased.

15. The electrosurgical generator according to claim 9, wherein the power converter further includes a power inductor having a first inductance value.

16. The electrosurgical generator according to claim 15, wherein the ZVS inductor has a second inductance that is greater than the first inductance value.

* * * * *